(12) United States Patent
McCann et al.

(10) Patent No.: US 11,485,712 B2
(45) Date of Patent: Nov. 1, 2022

(54) INTERMEDIATES FOR PREPARING HERBICIDAL PYRIDAZINONES

(71) Applicant: FMC Corporation, Philadelphia, PA (US)

(72) Inventors: Stephen Frederick McCann, Newark, DE (US); Thomas Martin Stevenson, Newark, DE (US)

(73) Assignee: FMC Corporation, Philadelphia, PA (US)

( * ) Notice: Subject to any disclaimer, the term of this patent is extended or adjusted under 35 U.S.C. 154(b) by 0 days.

(21) Appl. No.: 17/280,568

(22) PCT Filed: Sep. 26, 2019

(86) PCT No.: PCT/US2019/053052
§ 371 (c)(1),
(2) Date: Mar. 26, 2021

(87) PCT Pub. No.: WO2020/069056
PCT Pub. Date: Apr. 2, 2020

(65) Prior Publication Data
US 2022/0033361 A1 Feb. 3, 2022

Related U.S. Application Data

(60) Provisional application No. 62/737,897, filed on Sep. 27, 2018.

(51) Int. Cl.
*C07D 237/22* (2006.01)
*C07D 237/16* (2006.01)

(52) U.S. Cl.
CPC ......... *C07D 237/22* (2013.01); *C07D 237/16* (2013.01)

(58) Field of Classification Search
CPC ............................ C07D 237/22; C07D 237/16
See application file for complete search history.

(56) References Cited

U.S. PATENT DOCUMENTS 3,496,160 A * 2/1970 Igari .................... C09B 62/165
534/632
3,661,904 A 5/1972 Iizuki et al.

4,978,665 A * 12/1990 Tanikawa ............. C07D 237/22
514/247
9,049,864 B2 6/2015 Burton et al.
9,693,556 B2 * 7/2017 Bhonoah .............. C07D 405/04

FOREIGN PATENT DOCUMENTS

GB 2519092 4/2015
WO 2015/168010 11/2015
WO 2017/074988 5/2017

OTHER PUBLICATIONS

Park, J Heterocyclic Chem, vol. 37(5), 2000, 5-10. (Year: 2000).*
Haider, Sci Synth, vol. 16, 2004, 125-164. (Year: 2004).*
International Search Report of corresponding PCT/US2019/053052 dated Mar. 26, 2021.
Park, et al., "Synthesis of Novel Acyclonucleosides Containing Pyridazine", Journal of Heterocyclic Chemistry, vol. 37, No. 1, Jan. 1, 2000, pp. 5-10, XP055641424.
Database PubChem compound online, May 20, 2016, XP002795585, retrieved from NCBI Database accession No. 119054678.
Database PubChem compound online, May 20, 2016, XP002795586, retrieved from NCBI Database accession No. 119054682.
Database PubChem compound online, May 20, 2016, XP002795587, retrieved from NCBI Database accession No. 119054681.
Database PubChem compound online, May 20, 2016, XP002795588, retrieved from NCBI Database accession No. 119054680.
Database PubChem compound online, May 20, 2016, XP002795589, retrieved from NCBI Database accession No. 119054679.

* cited by examiner

*Primary Examiner* — D Margaret M Seaman
(74) *Attorney, Agent, or Firm* — Xiaobin Ding; FMC Corporation

(57) ABSTRACT

Disclosed is a compound of Formula I, including N-oxides, and salts thereof, wherein $R^1$, $R^2$ and $R^3$ are defined as set forth in the disclosure. Also disclosed is a process for preparing a compound of Formula I. A compound of Formula I can also be used as a synthetic intermediate to prepare pyridazinone-based herbicides.

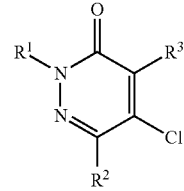

I

12 Claims, No Drawings

INTERMEDIATES FOR PREPARING HERBICIDAL PYRIDAZINONES

BACKGROUND OF THE INVENTION

The present disclosure provides pyridazinones and a process for preparing pyridazinones. The pyridazinones disclosed herein can be used as synthetic intermediates to prepare pyridazinone-based herbicides. WO 2015/168010 and WO 2017/074988 disclose herbicidal pyridazinones and synthetic intermediates used to prepare herbicidal pyridazinones. There exists a need for improved methods of preparing herbicidal pyridazinones.

SUMMARY OF THE INVENTION

In one aspect, the present disclosure provides a compound of Formula I and N-oxides or salts thereof,

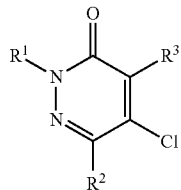

I wherein
  $R^1$ is $C_1$-$C_4$ alkyl or $C_3$-$C_6$ cycloalkyl;
  $R^2$ is Cl or $NH_2$;
  $R^3$ is Cl or $OR^4$; and
  $R^4$ is $C_1$-$C_4$ alkyl, $SO_2CF_3$ or $SO_2$ (4-Me-Ph).

In another aspect, the present disclosure provides a process for preparing a compound of Formula I-A,

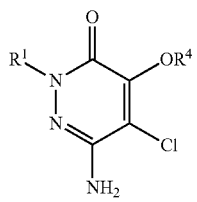

I-A wherein
  $R^1$ is $C_1$-$C_4$ alkyl or $C_3$-$C_6$ cycloalkyl; and
  $R^4$ is $C_1$-$C_4$ alkyl
comprising reacting a compound of Formula II

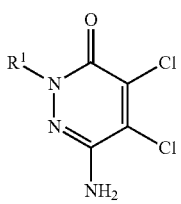

II wherein
  $R^1$ is $C_1$-$C_4$ alkyl or $C_3$-$C_6$ cycloalkyl
with an alkoxylating agent.

In another aspect, the present disclosure provides a process for preparing a compound of Formula I-B

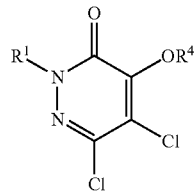

I-B wherein
  $R^1$ is $C_1$-$C_4$ alkyl or $C_3$-$C_6$ cycloalkyl; and
  $R^4$ is $C_1$-$C_4$ alkyl
comprising reacting a compound of Formula I-A, as set forth above, with an alkyl nitrite in the presence of CuCl or $CuCl_2$.

DETAILED DESCRIPTION OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a process or method that comprises a list of elements is not necessarily limited to only those elements but may include other elements not expressly listed or inherent to such composition process or method.

The transitional phrase "consisting of" excludes any element, step, or ingredient not specified. If in the claim, this phrase excludes materials other than those expressly recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a process or method that includes materials, steps, features, components, or elements, in addition to those literally disclosed, provided that these additional materials, steps, features, components, or elements do not materially affect the basic and novel characteristic(s) of the disclosure. The term "consisting essentially of" occupies a middle ground between "comprising" and "consisting of".

Where applicants have defined the disclosure or a portion thereof with an open-ended term such as "comprising," it should be readily understood that (unless otherwise stated) the description should be interpreted to also describe such a disclosure using the terms "consisting essentially of" or "consisting of" Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, the term "$C_1$-$C_6$ alkyl" includes straight-chain or branched alkyl groups having one to six carbon atoms, e.g., methyl, ethyl, n-propyl, i-propyl, or the different butyl, pentyl, or hexyl isomers. Likewise, the term "$C_1$-$C_4$ alkyl" includes straight-chain or branched alkyl having one to four carbon atoms, e.g., methyl, ethyl, n-propyl, i-propyl, or the different butyl isomers, and the term "$C_1$-$C_3$ alkyl" includes methyl, ethyl, n-propyl, and i-propyl. As used herein, the term "$C_3$-$C_6$ cycloalkyl" includes cyclopropyl, cyclobutyl, cyclopentyl and cyclohexyl. As used herein, the term "halogen" includes fluorine, chlorine, bromine and iodine.

The term "reacting" and the like refer to adding, contacting, or mixing two or more reagents under appropriate conditions to produce the indicated and/or the desired product. It should be appreciated that the reaction which produces the indicated and/or the desired product may not necessarily result directly from the combination of two reagents which were initially added, i.e. there may be one or more intermediates which are produced in the mixture which ultimately leads to the formation of the indicated and/or the desired product. Reacting can take place in the presence or absence of solvent, at a temperature above room temperature or below room temperature, under an inert atmosphere, etc.

Pressure is defined as the pressure measured relative to the ambient atmospheric pressure. The term "psig" means pounds per square inch gague.

The term "alkoxylating agent" as used herein refers to a chemical reagent used to add a $C_1$-$C_4$ alkoxy group to a compound. As used herein, the term "$C_1$-$C_4$ alkoxy" includes methoxy, ethoxy, n-propyloxy, isopropyloxy and the different butoxy isomers. Exemplary non-limiting alkoxylating agents include sodium methoxide and sodium ethoxide. Likewise, the term "methoxylating agent" as used herein refers to a chemical reagent used to add a methoxy group, i.e. $OCH_3$, to a starting compound. The term "alkyl nitrite" as used herein refers to a compound having the formula R—ONO, wherein R is a $C_1$-$C_6$ alkyl. Exemplary non-limiting alkyl nitrites include tert-butyl nitrite, amyl nitrite and n-butyl nitrite. When $R^4$ is "$SO_2$(4-Me-Ph)" this is alternatively defined as "$SO_2$(p-tolyl)."

Compounds of Formula I typically exist in more than one solid form. Thus, compounds of Formula I include all crystalline and non-crystalline forms of the compounds within the genus represented by Formula I. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability.

One skilled in the art will appreciate that a polymorph of a compound of Formula I can exhibit beneficial effects (e.g., suitability for improved solubility) relative to another polymorph or a mixture of polymorphs of the same compound of Formula I. Preparation and isolation of a particular polymorph of a compound of Formula I can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

Synthetic methods for the preparation of N-oxides of heterocycles and tertiary amines are well known by one skilled in the art. Exemplary procedures for preparing N-oxides include the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. Methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press. That said, one skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides.

One skilled in the art recognizes that under some process conditions, chemical compounds can be isolated in nonsalt or salt forms. Thus, a wide variety of salts of the compounds disclosed here can be isolated using the present process or processes depending on the base utilized in the method to prepare the compounds. Suitable salts include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Embodiments of the present disclosure include:

Embodiment A1

A compound of Formula I and N-oxides or salts thereof as described in the Summary of the Invention.

Embodiment A2

The compound of Embodiment A1 wherein $R^1$ is $C_1$-$C_4$ alkyl.

Embodiment A3

The compound of Embodiment A1 wherein $R^1$ is $C_3$-$C_6$ cycloalkyl.

Embodiment A4

The compound of any one of Embodiments A1 to A2 wherein $R^1$ is methyl or ethyl.

Embodiment A5

The compound of Embodiment A4 wherein $R^1$ is methyl.

Embodiment A6

The compound of any one of Embodiments A1 to A5 wherein $R^2$ is Cl.

Embodiment A7

The compound of any one of Embodiments A1 to A5 wherein $R^2$ is NH2.

Embodiment A8

The compound of any one of Embodiments A1 to A7 wherein $R^3$ is Cl.

Embodiment A9

The compound of any one of Embodiments A1 to A7 wherein $R^3$ is $OR^4$.

Embodiment A10

The compound of Embodiment A9 wherein $R^4$ is $C_1$-$C_4$ alkyl.

Embodiment A11

The compound of Embodiment A10 wherein $R^4$ is methyl, ethyl, n-propyl or i-propyl.

Embodiment A12

The compound of Embodiment A9 wherein $R^4$ is $SO_2CF_3$ or $SO_2$(4-Me-Ph).

Embodiment A13

A compound of Formula I in the Summary of the Invention that is a compound of Formula I-A

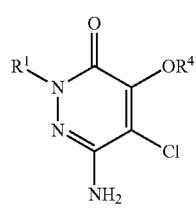

I-A wherein
$R^1$ is $C_1$-$C_4$ alkyl or $C_3$-$C_6$ cycloalkyl;
$R^3$ is $OR^4$; and
$R^4$ is $C_1$-$C_4$ alkyl.

Embodiment A14

A compound of Formula I in the Summary of the Invention that is a compound Formula I-B

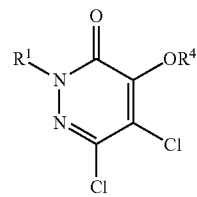

I-B wherein
$R^1$ is $C_1$-$C_4$ alkyl or $C_3$-$C_6$ cycloalkyl; and
$R^4$ is $C_1$-$C_4$ alkyl.

Embodiment A15

A compound of Formula I in the Summary of the Invention that is a compound Formula I-C

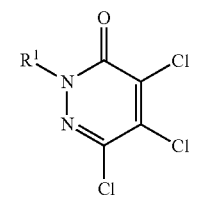

I-C wherein
$R^1$ is $C_1$-$C_4$ alkyl or $C_3$-$C_6$ cycloalkyl.

Embodiment A16

A compound of any one of Embodiments A1, A2, A4 or A6 through A15 wherein $R^1$ is methyl.

Embodiment A17

A compound of any one of Embodiments A1 through A5 or A-6 through A16 wherein $R^2$ is other than Cl (i.e. is other than a compound of Formula I-B or I-C).

Embodiment A18

A compound of Embodiment A1 that is other than 4,5,6-trichloro-2-methyl-3(2H)-pyridazinone (CAS No. 37648-42-3) and 6-amino-4,5-dichloro-2-methyl-3(2H)-pyridazinone (CAS No. 25717-64-0).

Embodiment B1

A process for preparing a compound of Formula I-A as described in the Summary of the Invention.

Embodiment B2

The process of Embodiment B1 wherein $R^1$ is $C_3$-$C_6$ cycloalkyl.

Embodiment B3

The process of Embodiment B1 wherein $R^1$ is $C_1$-$C_4$ alkyl.

Embodiment B4

The process of Embodiment B1 or B3 wherein $R^1$ is methyl.

Embodiment B5

The process of any one of Embodiments B1 to B4 wherein the reacting is performed in a suitable solvent.

Embodiment B6

The process of Embodiment B5 wherein the suitable solvent is methanol or dioxane.

Embodiment B7

The process of any one of Embodiments B1 to B6 wherein the reacting is performed at a temperature at or below 0° C.

Embodiment B8

The process of any one of Embodiments B1 to B6 wherein the reacting is performed at a temperature above 0° C.

Embodiment B9

The process of any one of Embodiments B1 to B8 wherein the alkoxylating agent is sodium methoxide or potassium methoxide.

Embodiment B10

The process of any one of Embodiments B1 and B3 to B9 wherein $R^1$ is methyl.

Embodiment B11

The process of any one of Embodiments B1 to B10 wherein the compound of Formula I-A is isolated.

Embodiment C1

A process for preparing a compound of Formula I-B as described in the Summary of the Invention.

Embodiment C2

The process of Embodiment C1 wherein $R^1$ is $C_3$-$C_6$ cycloalkyl.

Embodiment C3

The process of Embodiment C1 wherein $R^1$ is $C_1$-$C_4$ alkyl.

Embodiment C4

The process of any one of Embodiments C1 or C3 wherein $R^1$ is methyl.

Embodiment C5

The process of any one of Embodiments C1 to C4 wherein $R^4$ is methyl or ethyl.

Embodiment C6

The process of any one of Embodiments C1 to C5 wherein the reacting is performed in a suitable solvent.

Embodiment C7

The process of Embodiment C6 wherein the suitable solvent is acetonitrile.

Embodiment C8

The process of any one of Embodiments C1 to C7 wherein the reacting is performed at a temperature at or below 0° C.

Embodiment C9

The process of any one of Embodiments C1 to C7 wherein the reacting is performed at a temperature above 0° C.

Embodiment C10

The process of any one of Embodiments C1 through C9 wherein the alkyl nitrite is tert-butyl nitrite.

Embodiment C11

The process of any one of Embodiments C1 to C6 or C9 to C10 wherein the reacting is performed at a temperature between 0° C. and 180° C.

Embodiment C12

The process of Embodiment C11 wherein the reacting is performed at a temperature between 0° C. and 80° C.

Embodiment C13

The process of any one of Embodiments C1, C3 or C5 through C12 wherein $R^1$ is methyl.

Embodiment C14

The process of any one of Embodiments C1 to C13 wherein the compound of Formula I-B is isolated.

Embodiment D1

A process for preparing a compound of Formula I-C as described in the Summary of the Invention.

Embodiment D2

The process of Embodiment D1 wherein $R^1$ is $C_3$-$C_6$ cycloalkyl.

Embodiment D3

The process of Embodiment D1 wherein $R^1$ is $C_1$-$C_4$ alkyl.

Embodiment D4

The process of Embodiment D1 or D3 wherein $R^1$ is methyl.

Embodiment D5

The process of any one of Embodiments D1 to D4 wherein the reacting is performed neat or in a suitable solvent.

Embodiment D6

The process of Embodiment D5 wherein the suitable solvent is acetonitrile.

Embodiment D7

The process of Embodiment D5 wherein the reacting is performed neat.

Embodiment D8

The process of any one of Embodiments D1 to D7 wherein the reacting is performed at a temperature between 80° C. and 150° C.

Embodiment D9

The process of any one of Embodiment D8 wherein the reacting is performed at a temperature between 100° C. and 140° C.

Embodiment D10

The process of Embodiment D8 wherein the reacting is performed at a temperature between 120° C. and 140° C.

Embodiment D11

The process of Embodiment D8 wherein the reacting is performed at a temperature between 100° C. and 120° C.

Embodiment D12

The process of Embodiment D8 wherein the reacting is performed at a temperature of 120° C.

Embodiment D13

The process of Embodiment D8 wherein the pressure at 100° C. is up to 117 psig (807 kPa).

Embodiment D14

The process of Embodiment D8 wherein the pressure at 120° C. is up to 150 psig (1034 kPa).

Embodiment D15

The process of Embodiment D8 wherein the pressure at 140° C. is up to 223 psig (1538 kPa).

Embodiment D16

The process of any one of Embodiments D1 to D9 wherein the reacting is in the presence of N,N-dimethylformamide.

Embodiment D17

The process of Embodiment D10 wherein the reacting is in the presence of N,N-dimethylformamide between 10 mol % and 100 mol %.

Embodiment D18

The process of Embodiment D11 wherein the reacting is in the presence of N,N-dimethylformamide between 20 mol % and 30 mol %.

Embodiment D19

The process of any one of Embodiments D1 to D12 wherein the compound of Formula I-C is isolated.

Embodiments A1 through A18, B1 through B11, C1 through C14 and D1 through D19 and any other Embodiment or Embodiments described herein can be combined in any manner.

A compound of Formula I-B can be prepared by the reaction of a trichloropyridazinone compound of Formula I-C with either sodium or potassium alkoxide in a solvent such as 1,4-dioxane or tetrahydrofuran at temperatures ranging from 0° C. up to the reflux temperature of the solvent as depicted in Scheme 1. The preparation of a compound of Formula I-C is described in *J. Het. Chem.* 1972, vol. 9, p. 471.

Scheme 1

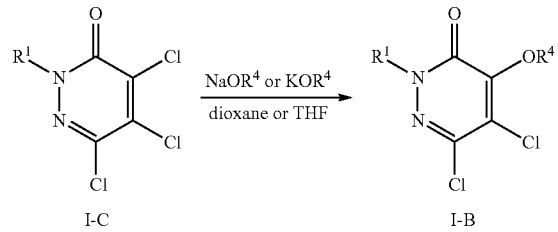

As shown in Scheme 2, a compound of Formula I-C can alternatively be prepared by the chlorination of a compound of Formula 3 (wherein M is H, Na or K) using one or more chlorinating reagents, such as $POCl_3$, $PCl_3$, $PCl_5$ and combinations thereof. Typically, the reaction is conducted neat in the chlorinating reagent, or in the combination of chlorinating reagents, at 80° C. to 150° C., preferably around 100° C.

Scheme 2

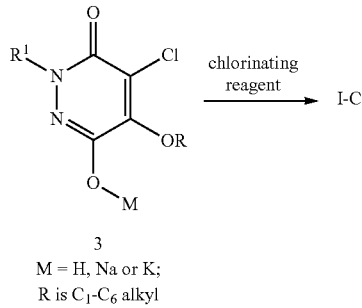

M = H, Na or K;
R is $C_1$-$C_6$ alkyl

As shown in Scheme 3, a compound of Formula 3 can be prepared by treatment of a compound of Formula 4 with sodium or potassium alkoxide in an organic solvent, such as methanol, ethanol, isopropanol or tetrahydrofuran. Typically, in alcoholic solvents the reaction is conducted at 60° C. to 150° C., preferably 70° C. to 80° C. Typically, in non-alcoholic solvents, such as tetrahydrofuran, the reaction is conducted at 0° C. to 20° C., preferably 0° C. to 5° C. The method of Scheme 3 is illustrated in present Synthesis Example 3.

Scheme 3

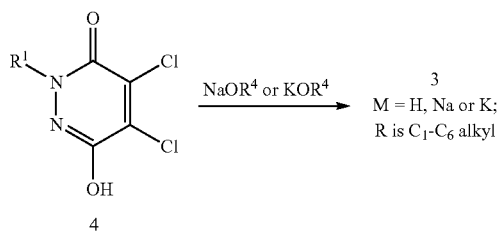

A compound of Formula I-C can also be prepared from maleic anhydride in two steps as described in WO 8704321 A2 and JP47024029B and as shown in Scheme 4. Alternative conditions for the second reaction of Scheme 4 include using one or more chlorinating reagents, such as $POCl_3$, $PCl_3$, $PCl_5$ and combinations thereof in the presence of N,N-dimethylformamide in a sealed reactor. Typically, the reaction is conducted neat at 80° C. to 150° C., preferably 100° C. to 120° C. The amount of N,N-dimethylformamide can be from 10 mol % to 100 mol %, preferably 20 mol % to 30 mol %. The reaction can be conducted neat or in an organic solvent, such as acetonitrile. The second reaction of Scheme 4 is illustrated in present Synthesis Example 4.

Scheme 4

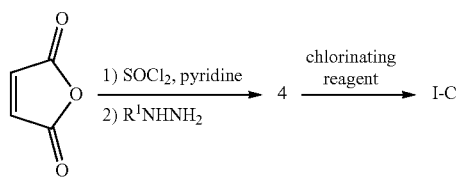

A compound of Formula I-B can be prepared using the procedures depicted in Scheme 5. An amino-pyridazinone compound of Formula I-A can be treated with an alkyl nitrite, such as tert-butyl nitrite or isoamyl nitrite, and either CuCl or $CuCl_2$ in a solvent such as acetonitrile at temperatures ranging from 0° C. to the refluxing temperature of the solvent. An analogous procedure can be found on page 82 in WO2010/009183. Alternative conditions for the reaction in Scheme 5 include reacting a compound of Formula I-A with sodium nitrite and concentrated hydrochloric acid, optionally in a solvent such as acetonitrile. An analogous procedure can be found on page 223 in WO2012/091156.

Scheme 5

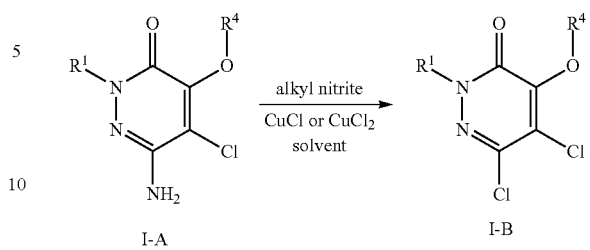

The preparation of a compound of Formula I-A can be achieved by the treatment of a compound of Formula 5 with sodium alkoxide in dioxane as depicted in Scheme 6. In Scheme 5, sodium alkoxide (1.0-1.5 molar equivalents), either as a solid or as a 25% alcoholic solution, can be added to a solution of Compound 5 in dioxane, and the resulting mixture can be stirred at a temperature of preferably 10° C. up to the reflux temperature of the solvent. The preparation of a compound of Formula 5 is described in *J. Het. Chem.* 1996, vol. 33, p. 1915. See also *J. Het. Chem.* 1996, vol. 33, p. 1579.

Scheme 6

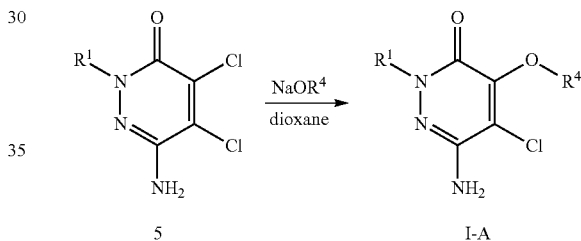

Without further elaboration, it is believed that one skilled in the art using the preceding description can utilize the present disclosure to its fullest extent. The following non-limiting Examples are illustrative of the disclosure. Steps in the following Examples illustrate a procedure for each step in an overall synthetic transformation, and the starting material for each step may not have necessarily been prepared by a particular preparative run whose procedure is described in other Examples or Steps.

The compounds and processes described for preparing a compound of Formula I, I-A, I-B and I-C herein are useful for preparing herbicidal pyridazinones. Notably where a compound of Formula I

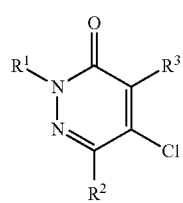

wherein
  $R^1$ is $C_1$-$C_4$ alkyl or $C_3$-$C_6$ cycloalkyl;
  $R^2$ is Cl;
  $R^3$ is Cl or $OR^4$; and
  $R^4$ is $C_1$-$C_4$ alkyl, $SO_2CF_3$ or $SO_2$(4-Me-Ph);
can be reacted with a compound of Formula III

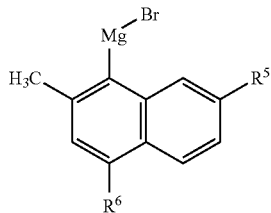

III wherein
  $R^5$ is H, F, Cl or $CH_3$; and
  $R^6$ is H or Cl;
under suitable conditions to provide a compound of Formula IV

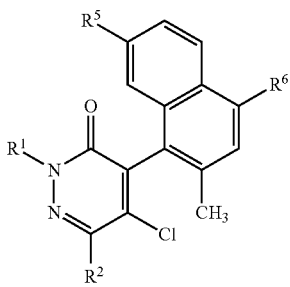

IV wherein
  $R^1$ is $C_1$-$C_4$ alkyl or $C_3$-$C_6$ cycloalkyl;
  $R^2$ is Cl;
  $R^5$ is H, F, Cl or $CH_3$; and
  $R^6$ is H or Cl.

A compound of Formula IV can further be reacted with a methoxylating agent to prepare a compound of Formula V

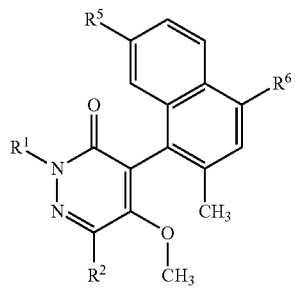

V wherein
  $R^1$ is $C_1$-$C_4$ alkyl or $C_3$-$C_6$ cycloalkyl;
  $R^2$ is Cl;
  $R^5$ is H, F, Cl or $CH_3$;
  $R^6$ is H or Cl; and A compound of Formula V can be reacted with a demethylating agent (such as morpholine) to prepare a compound of Formula VI

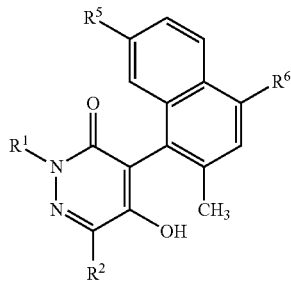

VI wherein
  $R^1$ is $C_1$-$C_4$ alkyl or $C_3$-$C_6$ cycloalkyl;
  $R^2$ is Cl;
  $R^5$ is H, F, Cl or $CH_3$; and
  $R^6$ is H or Cl.

Preferably in the compounds of Formulae I, IV, V and VI; $R^1$ is methyl. Preferably in the compounds of Formulae IV, V and VI; $R^5$ is H. Preferably in the compounds of Formulae IV, V and VI; $R^5$ is $CH_3$. Preferably in the compound of Formulae IV, V and VI; $R^6$ is H. Compounds of Formula VI are known from WO 2015/168010 to possess herbicidal activity.

Without further elaboration, it is believed that one skilled in the art using the preceding description can utilize the present disclosure to its fullest extent. The following non-limiting Examples are illustrative of the disclosure. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ unless otherwise indicated; "s" means singlet and "br s" means broad singlet.

Synthesis Example 1

Preparation of 6-amino-5-chloro-4-methoxy-2-methyl-3(2H)-pyridazinone

A solution of sodium methoxide in methanol (4.8 mL of a 4.4 M solution, 21.0 mmol) was added to a suspension of 6-amino-4,5-dichloro-2-methyl-3(2H)-pyridazinone (3.70 g, 19.1 mmol) and dioxane (95 mL, anhydrous) with ice-water bath cooling. The resulting suspension was stirred at ambient temperature for 3 h and was then poured into a saturated aqueous ammonium chloride solution (150 mL) and the resulting mixture was extracted with methylene chloride (150 mL). The aqueous layer was extracted two more times with methylene chloride and the combined organic extracts were dried over anhydrous magnesium sulfate, filtered and concentrated to give 3.45 g of the title compound as a yellow semi-solid. 1H NMR (500 MHz) δ 4.34 (br s, 2H), 4.29 (s, 3H), 3.60 (s, 3H).

Synthesis Example 2

Preparation of 5,6-dichloro-4-methoxy-2-methyl-3(2H)-pyridazinone

To a solution of 6-amino-5-chloro-4-methoxy-2-methyl-3(2H)-pyridazinone (i.e. the product obtained in Synthesis Example 1, 529 mg, 2.8 mmol), copper(II) chloride (618 mg, 4.6 mmol) and acetonitrile (8 mL, anhydrous) was added tert-butyl nitrite (0.48 mL, 90% by weight, 3.6 mmol) with ice-water bath cooling. The resulting mixture was stirred at ambient temperature for 1 h and was then partitioned between ethyl acetate and a saturated aqueous ammonium chloride solution. The organic layer was washed with a saturated aqueous ammonium chloride solution, dried over anhydrous magnesium sulfate, filtered and concentrated to give 0.51 g of the title compound as a yellow semi-solid.

$^1$H NMR (500 MHz) δ 4.33 (s, 3H), 3.74 (s, 3H).

Synthesis Example 3

Preparation of 2-methyl-4,5,6-trichloro-3(2H)-pyridazinone

A mixture of 4,5-dichloro-1,2-dihydro-1-methyl-3,6-pyridazinedione (10 g, 51 mmol), phosphorous oxychloride (8.4 g, 55 mmol) and N,N-dimethylformamide (0.37 g, 5.1 mmol) was sealed in a pressure reactor, heated to 120° C. The reaction was agitated for 6 h. During the reaction, the reaction pressure increased by 150 psig (1034 kPa). The reaction was cooled to room temperature. Water (100 mL) was added to the resultant mixture, agitated for 1 h, filtered, washed with water (20 mL) and dried under vacuum. To the filtered solid was added hexanes (30 mL) at 5° C., filtered and dried to give 8.7 g of the title compound as a beige solid.

$^1$H NMR (500 MHz) δ 3.86 (s).

Synthesis Example 4

Preparation of 5,6-dichloro-4-methoxy-2-methyl-3(2H)-pyridazinone

To a solution of 2-methyl-4,5,6-trichloro-3(2H)-pyridazinone (i.e. the product obtained in Synthesis Example 3, 12 g, 56 mmol) in tetrahydrofuran (96 mL) at 1° C. was slowly added sodium methoxide (25% in methanol, 12.7 g, 59 mmol) over 30 min. The resulting mixture was warmed to room temperature over 30 min. Water (100 mL) was added. The organic layer was separated and concentrated to give 21 g of a beige solid. The solid was recrystallized from methanol/water (60 mL/60 mL) to yield 8.25 g of the title compound as a beige solid.

$^1$H NMR (500 MHz) δ 4.33 (s, 3H), 3.74 (s, 3H). Representative examples of synthetic intermediates useful in the preparation of herbicidal pyridazinones are shown in Table 1.

TABLE 1

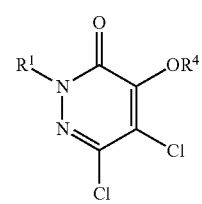

| $R^1$ | $R^2$ | $R^3$ |
|---|---|---|
| CH$_3$ | NH$_2$ | OCH$_3$ |
| CH$_3$ | Cl | OCH$_3$ |
| CH$_3$ | Cl | Cl |

All patents and publications cited herein are fully incorporated by reference in their entirety.

What is claimed is:

1. A compound of Formula I and N-oxides and/or salts thereof

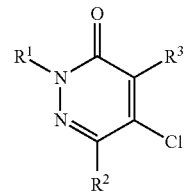

wherein
$R^1$ is $C_1$-$C_4$ alkyl or $C_3$-$C_6$ cycloalkyl;
$R^2$ is Cl or NH$_2$;
$R^3$ is OR$^4$; and
$R^4$ is $C_1$-$C_4$ alkyl, SO$_2$CF$_3$ or SO$_2$(4-Me-Ph).

2. The compound of claim 1 that is a compound of Formula I-A

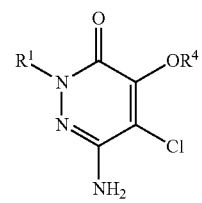

wherein
$R^1$ is $C_1$-$C_4$ alkyl or $C_3$-$C_6$ cycloalkyl; and
$R^4$ is $C_1$-$C_4$ alkyl.

3. The compound of claim 2 wherein
$R^1$ is $C_1$-$C_4$ alkyl; and
$R^4$ is methyl, ethyl, n-propyl or i-propyl.

4. The compound of claim 3 wherein
$R^1$ is methyl; and
$R^4$ is methyl.

5. The compound of claim 1 that is a compound of Formula I-B

I-B wherein
$R^1$ is $C_1$-$C_4$ alkyl or $C_3$-$C_6$ cycloalkyl; and
$R^4$ is $C_1$-$C_4$ alkyl.

6. The compound of claim 5 wherein
$R^1$ is $C_1$-$C_4$ alkyl; and
$R^4$ is methyl, ethyl, n-propyl or i-propyl.

7. The compound of claim 6 wherein
$R^1$ is methyl; and
$R^4$ is methyl.

8. A process for preparing a compound of Formula I-A

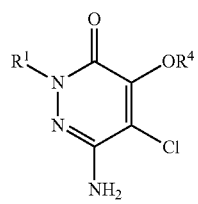

I-A wherein
  $R^1$ is $C_1$-$C_4$ alkyl or $C_3$-$C_6$ cycloalkyl; and
  $R^4$ is $C_1$-$C_4$ alkyl
comprising reacting a compound of Formula II

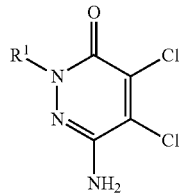

II wherein
  $R^1$ is $C_1$-$C_4$ alkyl or $C_3$-$C_6$ cycloalkyl
with an alkoxylating agent.

9. The process of claim 8 wherein $R^1$ is methyl.

10. A process for preparing a compound of Formula I-B

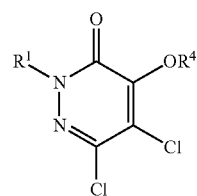

I-B wherein
  $R^1$ is $C_1$-$C_4$ alkyl or $C_3$-$C_6$ cycloalkyl; and
  $R^4$ is $C_1$-$C_4$ alkyl
comprising reacting a compound of Formula I-A

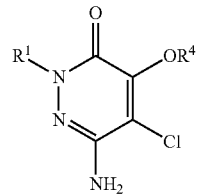

I-A wherein
  $R^1$ is $C_1$-$C_4$ alkyl or $C_3$-$C_6$ cycloalkyl; and
  $R^4$ is $C_1$-$C_4$ alkyl
with an alkyl nitrite in the presence of CuCl or $CuCl_2$.

11. The process of claim 10 wherein $R^1$ is methyl.

12. The process of claim 10 wherein $R^4$ is methyl.

* * * * *